United States Patent
Krill

(10) Patent No.: US 7,118,531 B2
(45) Date of Patent: Oct. 10, 2006

(54) INGESTIBLE MEDICAL PAYLOAD CARRYING CAPSULE WITH WIRELESS COMMUNICATION

(75) Inventor: Jerry A. Krill, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 303 days.

(21) Appl. No.: 10/669,484

(22) Filed: Sep. 24, 2003

(65) Prior Publication Data
US 2004/0122315 A1 Jun. 24, 2004

Related U.S. Application Data

(60) Provisional application No. 60/413,466, filed on Sep. 24, 2002.

(51) Int. Cl.
*A61B 5/00* (2006.01)
*A61B 1/04* (2006.01)
*A61M 25/00* (2006.01)

(52) U.S. Cl. ............ 600/309; 600/109; 600/302; 600/300; 604/19

(58) Field of Classification Search ............ 600/302, 600/109, 309, 300; 348/77, 718; 604/19
See application file for complete search history.

(56) References Cited

U.S. PATENT DOCUMENTS

| | | | |
|---|---|---|---|
| 4,672,963 A | | 6/1987 | Barken |
| 5,304,214 A | | 4/1994 | DeFord et al. |
| 5,515,853 A | * | 5/1996 | Smith et al. ............ 600/437 |
| 5,797,849 A | | 8/1998 | Vesely et al. |
| 5,807,258 A | | 9/1998 | Cimochowski et al. |
| 5,967,980 A | | 10/1999 | Ferre et al. |
| 6,053,873 A | | 4/2000 | Govari et al. |
| 6,056,695 A | | 5/2000 | Rupp et al. |
| 6,106,464 A | * | 8/2000 | Bass et al. ............ 600/439 |
| 6,246,898 B1 | | 6/2001 | Vesely et al. |
| 6,402,689 B1 | * | 6/2002 | Scarantino et al. ......... 600/300 |
| 6,632,175 B1 | * | 10/2003 | Marshall ................ 600/309 |
| 2002/0123672 A1 | * | 9/2002 | Christophersom et al. .. 600/300 |
| 2002/0198470 A1 | * | 12/2002 | Imran et al. ............ 600/587 |

OTHER PUBLICATIONS

Fantastic Voyage: Almost A Reality; Viacomm Internet Services Inc., CBS News Broadcast;New York, Jan. 7, 2001 http://www.cbsnews.com/stories/2001/01/07/tech/printable262207.shtml.

Wells. P. "Current status and future technical advances of ultrasonic imaging." IEEE Engineering in Medicine and Biology, Sep./Oct. 2000, pp. 14-20.

Zara, J., Bobbio, S., Goodwin-Johansson, S. & Smith, S. Intracardiac ultrasound scanner using a micromachine (MEMS) actuator, IEEE Transactions of Ultrasonics, Ferroelectrics, and Frequency Control, Jul. 2000, vol. 47, No. 4, pp. 984-993.

* cited by examiner

*Primary Examiner*—Eric F. Winakur
(74) *Attorney, Agent, or Firm*—Albert J. Fasulo, II

(57) ABSTRACT

A medical capsule is provided which includes at least a housing, transceiver, ultrasonic transducer(s), a power source, a microprocessor, and is capable of carrying a medical payload. The capsule is ingestible or implantible in a human or animal body and communicates wirelessly via ultrasonic signals with one or more transceivers attached to the outside of the body. The capsule payload can perform diagnostic, analytical, treatment or imaging functions and its position within the body can be accurately monitored. A wireless system employing the capsule and external transceiver can also include a remote monitoring station accessed by radio frequency electromagnetic signals. Further, collaborative activity among the internal capsules is enabled by an inter-capsule and capsule-to-external transceiver acoustic communications net.

12 Claims, 4 Drawing Sheets

INGESTIBLE MEDICAL PAYLOAD CARRYING CAPSULE WITH WIRELESS COMMUNICATION

CROSS-REFERENCE TO RELATED APPLICATIONS

This application claims the benefit of U.S. Provisional Application No. 60/413,466 filed Sep. 24, 2002, the contents of which are incorporated herein by reference.

BACKGROUND OF THE INVENTION

1. Field of the Invention

The present invention relates generally to a medical payload carrying capsule with wireless communication which can be swallowed for diagnostics, treatment, internal viewing and the like.

2. Description of the Related Art

Devices which are implantable or ingestible in the human body are known. For example, U.S. Pat. No. 6,400,338 discloses an implantable device with a passive integrated transponder which can be used for tracking the location of an animal or human into which it is implanted.

Various ingestible devices include miniature cameras for providing imaging of the interior of the stomach or colon to detect bleeding, polyps, and other conditions. Such devices provide an alternative to more invasive techniques such as colonoscopy or endoscopy.

What is needed is an ingestible device which can be wirelessly tracked and remotely controlled, and which can perform various medical functions to aid in the diagnosis, treatment, and/or imaging of the interior of a human or animal body.

SUMMARY OF THE INVENTION

A medical capsule is provided herein which comprises a housing having an interior space with a cargo bay area, a transceiver enclosed within said housing, at least one ultrasonic transducer electrically connected to the transceiver, a power supply enclosed within the housing and electrically connected to the transceiver, and a microprocessor unit for data processing and control, the microprocessor being electrically connected to the transceiver. The capsule is adapted to carry a medical payload in the cargo bay area including diagnostic devices, devices for treating a medical condition, and visualizing apparatus.

Multiple capsules can be used to monitor conditions in a living human or animal body, or to provide treatment or imaging functions. One or more external transceivers attached to the exterior surface of the body communicate via ultrasonic signals with the capsule(s). Collaborative activity among the internal capsules is enabled by an inter-capsule and capsule-to-external transceiver acoustic communication network.

BRIEF DESCRIPTION OF THE DRAWINGS

Various embodiments are described below with reference to the drawings wherein.

DESCRIPTION OF THE PREFERRED EMBODIMENTS

The invention herein provides a means for wireless communication between capsule ingested or implanted in a living body (human or animal) and an external network. The wireless communication is by means of ultrasound, generally in the range of 5–20 MHz, using miniature acoustic transducers. The capsule is capable of carrying a medical payload including one or more of diagnostic equipment, treatment means such as, for example, drug delivery systems, imaging equipment such as miniaturized cameras, or other such devices. In addition to miniature transducer(s), the capsule preferably also includes a microprocessor, and a power source (such as a battery). The capsule further includes a cargo bay area for the medical payload.

External acoustic transceivers can be positioned outside of the body and can interface with other communication equipment such as cellular phones or other wireless transceivers at distant locations. Preferably, the external transceivers are attached to or positioned in proximity to an exterior surface of the body. This allows medical data to be transmitted from the capsule to remote monitoring locations. It also allows control or other signals to be transmitted from the remote monitoring locations to the capsule. The attached external acoustic transceivers can also be adapted to monitor and command the ingested capsule(s). The subject can monitor his own data and the external attached transceivers can be adapted to track the location of the capsule(s) with high accuracy. Moreover, multiple capsules can be ingested and ultrasonically linked in a network within the body, e.g., to coordinate functions.

Figure 1:
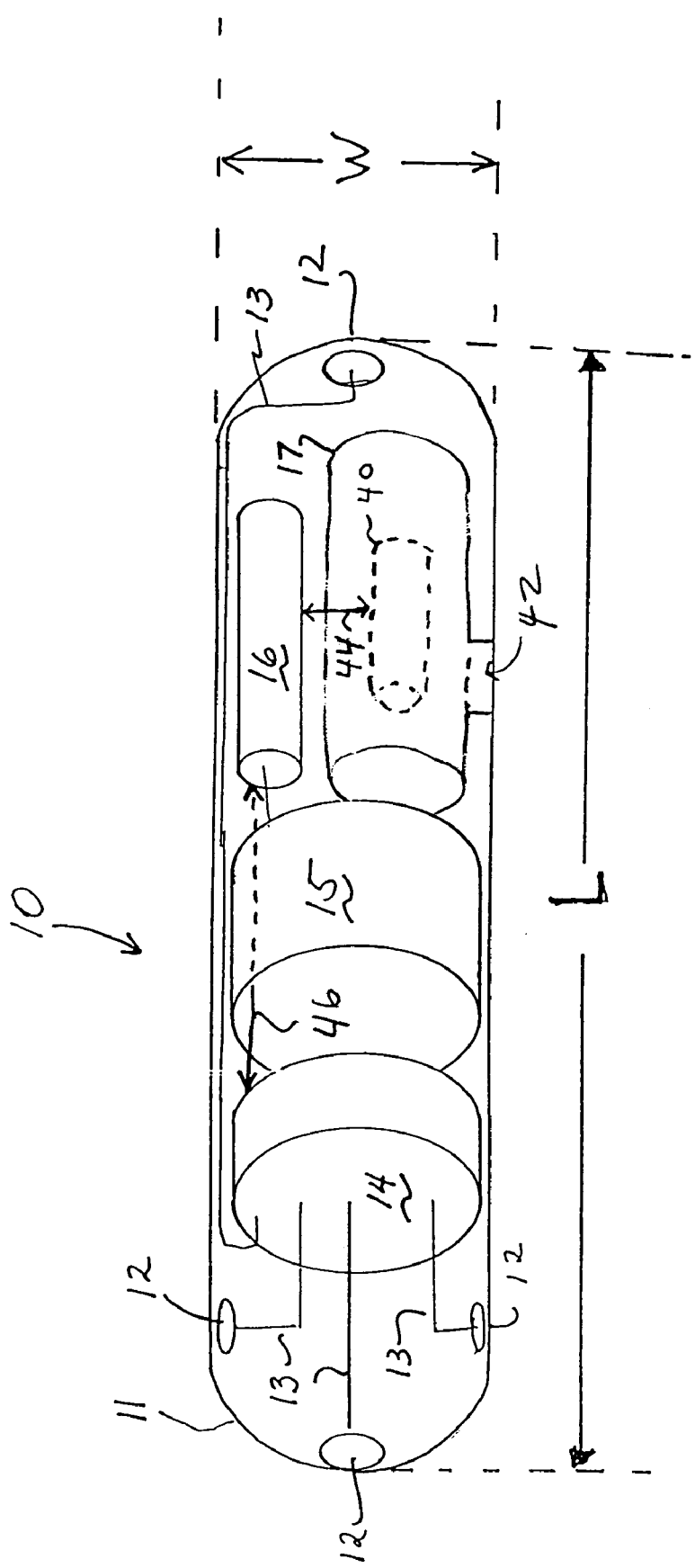
FIG. 1 is diagnostic view illustrating the capsule of the present invention.

Referring now to FIG. 1, a diagram of a capsule 10 is shown which includes at least an exterior housing 11 optionally fabricated from a biologically safe polymeric material such as, for example, polytetrafluoroethylene, polyethylene, acrylics and the like, or ceramics, or a metal, e.g., stainless steel. Capsule 10 is preferably of a size suitable to be swallowed, e.g., a capsule having a length preferably ranging from about 0.25 to about 1.0 inch, more preferably from about 0.5 to about 0.75 inches, and a width preferably ranging from about 0.0625 inch to about 0.375 inches, more preferably from about 0.125 inch to about 0.25 inch.

Capsule 10 includes a plurality of directional two-way ultrasonic acoustic transducers 12 which are attached by wire leads 13 to a transceiver and signal processor/generator unit 14. Transceiver 14 may optionally also include the ability to transmit and/or receive radio frequency communications. The plurality of directional transducers are arranged so that there is no transmission blockage from parts of the capsule and so that the assembly of combined inputs and outputs from them covers all angles, i.e., the assembly forms an omni-directional 'array'. With each transducer providing roughly a steradian or more of coverage, six transducers arrayed to each cover a different sector cover the full 2 pi steradians of solid angle coverage.

The encapsulated transducers 12 are preferably adapted to operate in the 5 MHz to 20 MHz ultrasonic range with a 1–2 MHz signal bandwidth. Higher frequencies (e.g., 15–20 MHz) are preferable for ultrasonic sensing resolution and dynamic range as well as image data transfers. Lower frequencies (e.g., 5–10 MHz) are preferable for reception of critical commands or data. Multiple band transmission is an option wherein multiple capsules are employed. The transducers 12 preferably operate on a power level of about 10 microwatts or less, and have a receiver sensitivity of from about −40 to about −50 dBm.

Suitable externally worn transducers and transducer arrays 20 (FIG. 2) for use in the present invention are commercially available. They are described, for example, in the article "Current Status and Future Technical Advances of Ultrasonic Imaging", by Peter Wells, IEEE Engineering in Medicine and Biology, September/October 2000, pages 14–20, the contents of which are incorporated by reference herein. The prototype miniature ultrasonic transducers 13 and transceivers 14 suitable for use in the present invention are reported in the IEEE Transactions of Ultrasonics, Ferroelectrics, and Frequency Control, July 2000, vol.47, No. 4, "Intracardiac Ultrasound Scanner Using a Micromachine (MEMS) Actuator", the contents of which are incorporated by reference herein.

Capsule 10 further includes a power source 15 which can be, e.g., a battery or a capacitor. Power source 15 powers the transceiver unit 14 as well as other electrically powered equipment in the capsule 10.

Microprocessor 16 advantageously performs command and control functions as well as data processing. More specifically, the microprocessor 'chip' performs the following functions: maintaining communications connectivity (e.g., controlling network participation), reading and responding to input messages via the transceiver and acoustic array, operating the payload mechanisms on command, recording and packaging payload measurements such as biochemical readings and imagery for transmission to the external transceiver (20), and transmitting capsule status including present activity and battery charge.

Capsule 10 further includes a cargo bay 17 within which is positioned a medical payload 40. The medical payload can be a microlaboratory device which can perform diagnostic functions such as testing the surrounding matter or fluid for pH (alkalinity or acidity), the presence of blood, toxins, microorganisms, or the presence or concentration of various salts, minerals or other selected materials. For example, cargo bay 17 can include a microfluidic device for microanalysis. Such microfluidic devices are known and commercially available. The housing 11 would include an aperture/inlet 42 or other access means in fluid communication with the interior of cargo bay 17 in the event that surrounding fluid would be introduced into the capsule 10 for analysis. Other types of diagnostic devices suitable for use in capsule 10 include means for measuring a condition of the body, e.g.,a thermometer for measuring body temperature, or means for monitoring sound, such as a microphone or other detection equipment, for monitoring heart beat rate, breathing, and the like. For example, the capsule can emit signals the timing of which is dependent upon the ambient temperature. Sounds can be digitized and transmitted via ultrasonic signals to the external transceiver(s) 20.

Capsule 10 includes an optional interface 44 for electrically coupling device 40 to processor 16. Interface 44 includes a connector having conductive pins and/or sockets, and in some configurations, actuator mechanisms, configured to mechanically couple device 40 to cargo bay 17, and electrically couple device 40 to processor 16. The connector preferably provides an easily removable connection between a connector on device 40 and capsule 10 so that device 40 may be easily plugged into and removed from cargo bay 17. Interface 44 includes conductive traces for carrying data signals and commands between device 40 and processor 16. Device 40 can transmit data collected or conditions sensed to processor 16 over signal interface 44. In turn, processor 16 can transmit such data to transceiver 14 over another electrical interface 46 for carrying data and commands between the processor and the transceiver.

Treatment devices can also be carried by capsule 10. For example, cargo bay 17 can contain a supply of a treatment medication which, upon command, is released into the surrounding fluid or tissue by means of a metered pumping mechanism (e.g., a mechanical or chemical pump). This would be advantageous to release medications which might be adversely affected by the digestive environment of the stomach. For example, the release of the medication can be timed to bypass the stomach and occur when the capsule has reached the small intestine. Medically efficacious materials which can be carried by the capsule include, for example, antibiotics, antiviral compounds, chemotherapeutic agents, nutriments (e.g. vitamins, minerals, enzymes), radio isotopes, dyes, tracers, radio opaque materials, growth factors, hormones, steroids, and the like.

Capsule 10 can also optionally include miniaturized visualizing apparatus such as an optical camera and optionally a light source (e.g., from a LED or flash unit). The images can be encoded by the microprocessor 16 and digitally transmitted to a remote receiver unit external to the body. Alternatively, the cargo bay 17 can include a transducer with a pulser driver for internal acoustic pulse illumination and external high resolution sonogram imaging and detection. The present invention allows the flash to be carried by one capsule and other capsules to capture the image from multiple aspected, triggered through the acoustic communications network. In this way unique perspectives can be gained in the imagery, e.g., via back-lighting or three-dimensional image construction. The nominal 1 MHz acoustic signal bandwidth is consistent with the relatively high data rate requirement for transmitting imagery.

Figure 2:
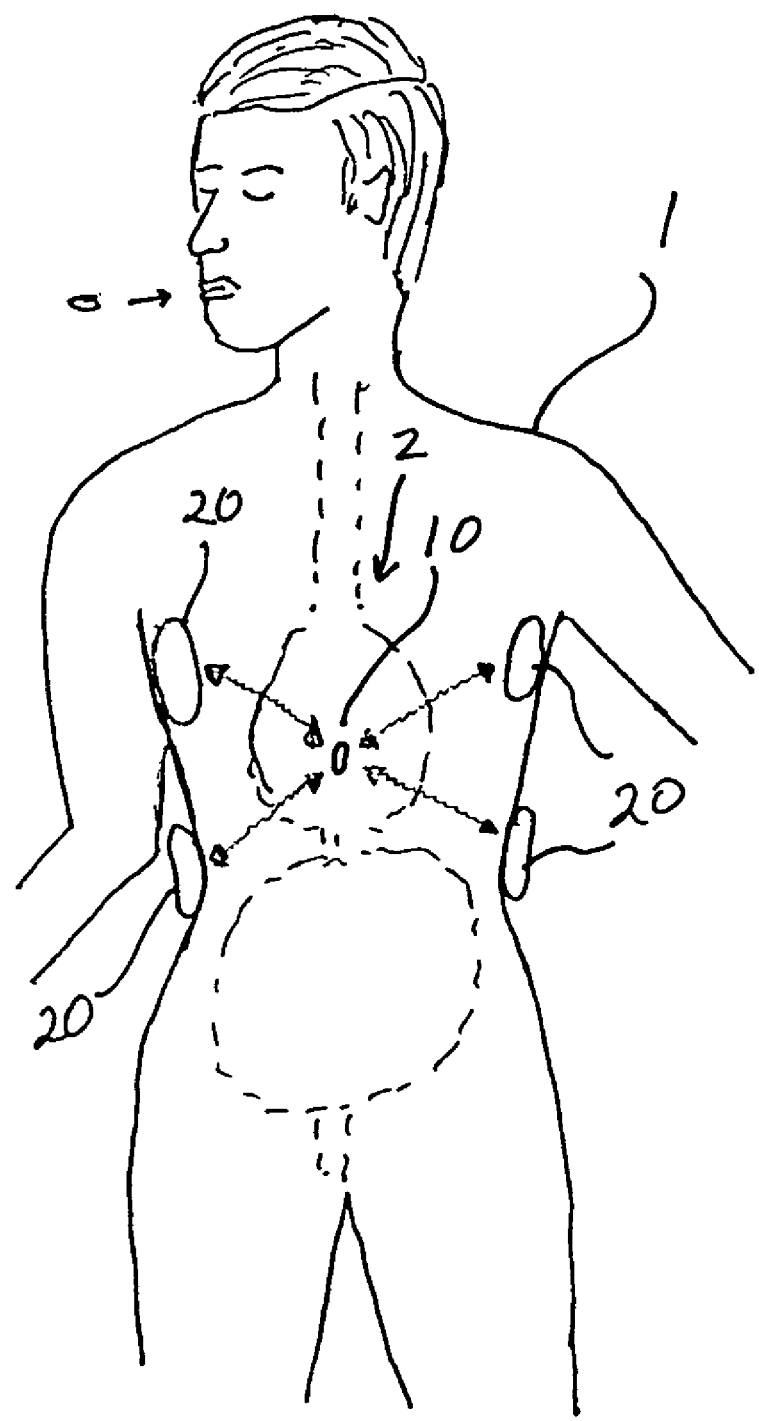
FIG. 2 is a diagrammatic view illustrating an arrangement of transceivers for monitoring the positioning of the capsule in a human body.

Referring now to FIG. 2, a capsule 10 is ingested by, for example, a human subject 1, and enters the alimentary system 2 of the human subject. A plurality of external transceivers 20 are attached to the exterior surface of the body of subject 1 in various locations around the torso of the subject. By sending and receiving coded ultrasonic signals to the capsule 10, and by determining the strength of the signals, the location of the capsule 10 in the body of the subject 1 can be determined and tracked as it moves through the alimentary system 2. The location of the capsule 10 can be determined by, for example, measuring the angle of the signal received from the capsule by each of several external transceivers with directional acoustic arrays so that combining angles results in tracking of the capsule location in the body by triangulation. Moreover, various coded commands and/or information can be transmitted to or received from the capsule 10.

The attenuation of ultrasonic waves depends upon the type of tissue through which the waves pass as well as the frequency of the waves. Referring to Table 1, the higher the frequency, the more the attenuation. Muscle, fat, and blood are characterized by less attenuation than bone or lungs.

TABLE 1

(Attenuation in dB through 10 cm of tissue)

| Frequency | Muscle/Fat/Blood | Bone | Lung |
|---|---|---|---|
| 20 MHz | 126 dB | — | — |
| 10 MHz | 63 dB | — | — |
| 5 MHz | 31.5 dB | 1,000 dB | 2050 dB |

Use of a plurality of external transceivers 20 and/or a plurality of capsules 10 can compensate for reduction of signal strength in high attenuation areas as an acoustic form of 'diversity reception' as it is known in telecommunications.

Figure 3:
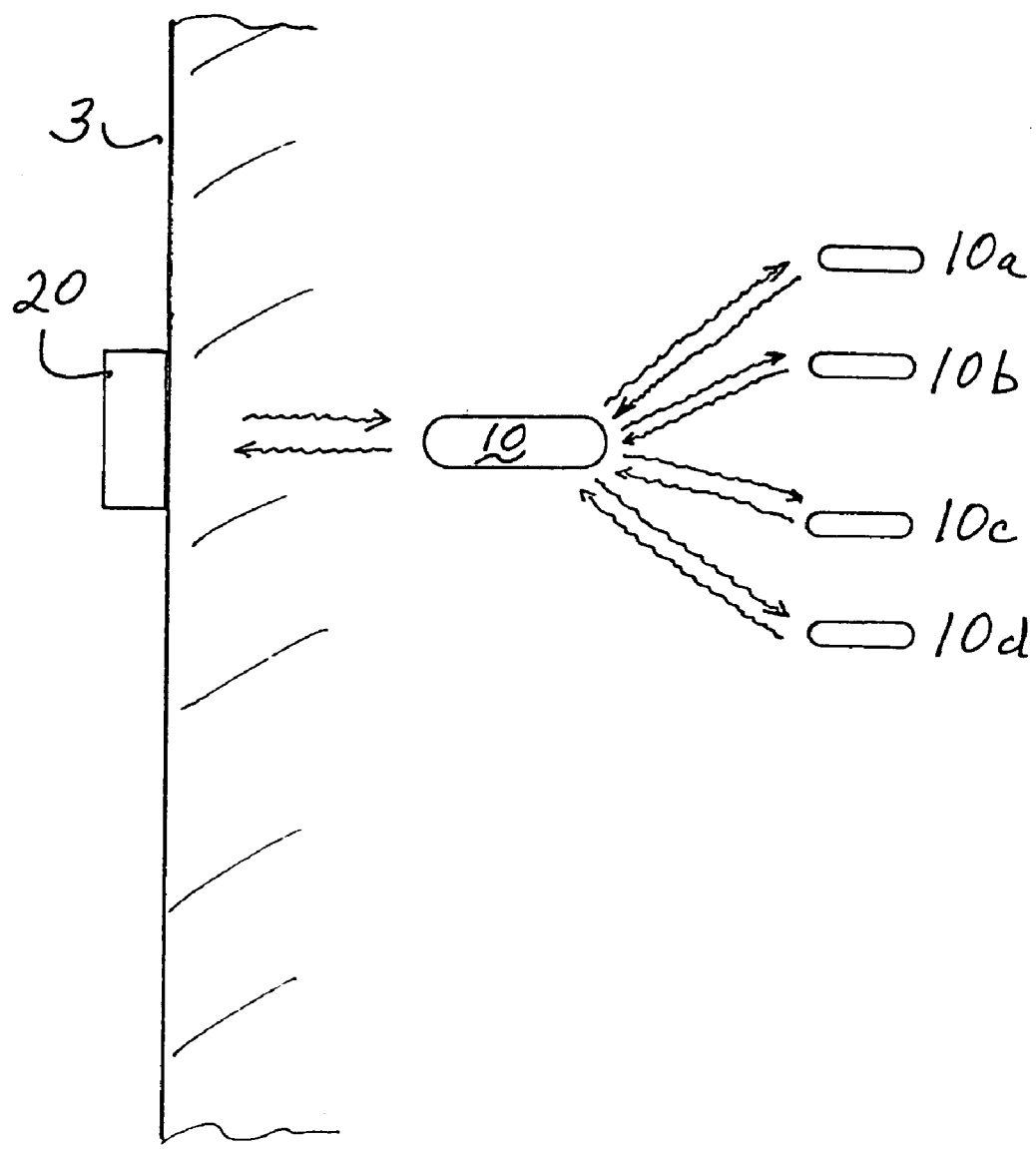
FIG. 3 is a diagrammatic view illustrating a multi-capsule communication network.

Referring now to FIG. 3, a system is shown wherein external transceiver 20 is attached to the exterior surface 3 of a body. A master or primary capsule 10 communicates by means of an ultrasonic signal with external transceiver 20. Moreover, one or more auxiliary capsules 10a, 10b, 10c, and 10d provide functional capabilities. For example, in one embodiment, external transceiver communicates with primary capsule 10, which carries a flash payload for illuminating the internal body tissue with optical, infrared, or ultrasonic flashes upon command from external transceiver 20. The auxiliary capsules 10a, 10b, 10c, 10d provide imaging capability with, for example, optical receivers or acoustic transceivers which receive and analyze ultrasonic flash or pulse signals from the primary capsule 10.

In another embodiments one or more auxiliary capsules 10a, 10b, 10c, 10d carry a medically efficacious material which is released upon command from primary capsule 10. Primary capsule 10 performs a relay function to relay the command from the external transceiver 20.

In yet another embodiment, one or more auxiliary capsules 10a, 10b, 10c, 10d have sensing equipment (e.g., microlaboratory) to perform analytical functions or temperature or sound detectors for monitoring various physiological conditions at various locations in the body.

Figure 4:
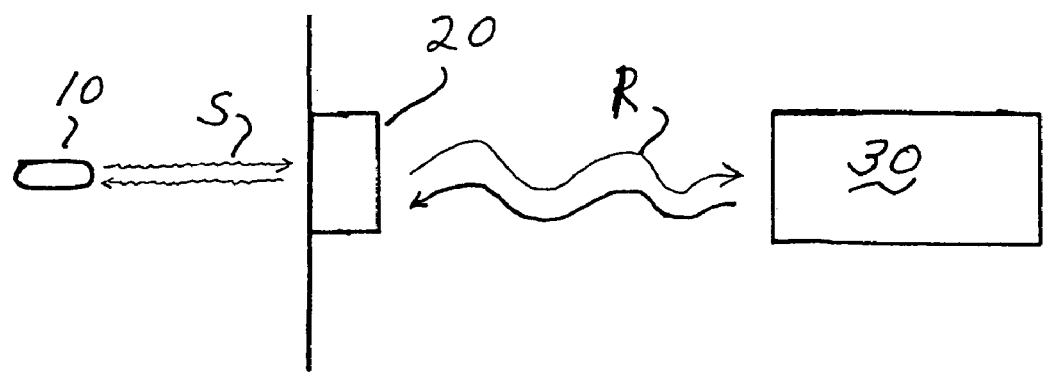
FIG. 4 is a diagrammatic view illustrating a system employing the capsule of the present invention which includes remote monitoring by means of radio telemetry.

Referring now to FIG. 4, a system which employs remote monitoring and communication is illustrated wherein capsule 10 positioned inside the body communicates via ultrasonic signals S with external transceiver 20 attached to the exterior surface of the body. Transceiver 20 also possesses means for communicating via radio frequency electromagnetic signals with a remote medical monitoring station 30. Optionally, multiple capsules 10, transceivers 20 and/or remote monitoring stations 30 can be employed in a communication network linked by wireless communications such as cellular phone or PDA services, or can be interfaced with an optical fiber network. The capsule(s) 10 can, for example, monitor the physiological condition of the body and transmit the data to the external transceiver(s) 20. The external transceiver(s) 20 can be programmed to collect data and recognize medical conditions which require attention and/or treatment (e.g., change in heart rate, breathing, body temperature etc.) and issue commands to the capsule to take remedial action (e.g., deployment of medically efficacious drugs) while sending signals to the remote medical monitoring station(s) 30 to alert medical personnel as to the medical condition.

Various procedures may be employed to facilitate the communication between capsules 10 and the external transceivers 20. In one procedure the external transceiver serves as a controller and calls each capsule 10 using a broad beam for transmission. The transmitted signal contains the capsules' address in a message header or is transmitted at a unique acoustic frequency channel associated with that capsule. The capsule receives and decodes the data, processes the data, and responds to the external transceiver 20 commands by, for example, sending data to the transceiver 20 or by emitting one or more ultrasonic pulses to enable the transceiver 20 to locate the position of the capsule 10 by standard direction finding techniques.

In another procedure, time division multiplexing, the external control transceiver 20 and capsules 10 each transmit in turn according to a prescribed time slot sequence. Optionally the capsules 10 and/or transceiver 20 would include clocks, or the external transceiver could transmit acoustic timing "ticks" to delineate time slots for synchronization.

The capsules 10 can communicate among themselves directly. But relaying capsule-to-capsule information through the external transceiver 20 takes advantage of the larger acoustic aperture and transmitting power of the transceiver 20.

Alternatively, in a two capsule "handshake procedure", (as it is known in network communications) a first capsule can periodically initiate transmission and a second capsule can respond directly to the first capsule by acknowledging receipt of the signal and by performing the requested function.

In another procedure each capsule is set with a unique identity (ID) address on a common acoustic frequency channel. One capsule is set, optionally on command from the controller, to broadcast a message to all other capsules. The capsule in the next identity address number in the sequence initiates a message broadcast transmission next, and so on, so that after the capsule with the nth ID address number in the sequence has broadcast, the capsule with the n+1$^{st}$ address number broadcasts next. This continues in succession until the maximum ID number is reached, at which time the capsule with the lowest ID number transmits and the sequence of broadcast transmissions begins again. If a capsule does not receive a transmission, and so, does not transmit, the next-in-sequence capsule transmits after a fixed delay.

In yet another procedure a number of capsules could operate on separate networks in which the capsules only respond to special code types—e.g., numbers ending in 6 or odd numbers. Alternatively, the above poll approach could occur on separate acoustic frequency channels. In this way on set of capsules performing one function can interact independently of another set of capsules performing a different function.

Data transmission between the electronic components of a capsule or between one capsule and another capsule or one capsule and an external transceiver can be by serial or parallel data transmission. However, serial data interfacing is preferred because it requires less power than parallel interfacing.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:
1. A medical capsule comprising:
   a housing configured and dimensioned to be ingestible and/or implantable in an animal body, the housing having an interior space with a cargo bay area and an opening into the cargo bay area;

a payload device, within the cargo bay area, selected from the group consisting of medical diagnostic devices, devices for treating a medical condition and visualizing apparatus;

a transceiver enclosed within said housing;

at least one ultrasonic transducer electrically connected to the transceiver;

a power supply enclosed with the housing and electrically connected to the transceiver;

a microprocessor unit for data processing and control, said microprocessor being electrically connected to the transceiver; and an interface for mechanically coupling the payload device to the cargo bay area and electrically coupling the payload device to the microprocessor so as to carry signals between the microprocessor and the payload device, the interface including a connector configured to provide a removable connection between the cargo bay area and the payload device so that the payload device can be plugged into and removed from the cargo bay area.

2. The capsule of claim 1, wherein the medical diagnostic devices include at least one microlaboratory device for analyzing body fluids for detecting and/or measuring blood, mineral, toxins and/or microorganisms.

3. The capsule of claim 2, wherein the microlaboratory device is a microfluidic device.

4. The capsule of claim 1, including an array of ultrasonic transducers to provide omni-directional coverage operable in the range of from about 5 MHz to about 20 MHz.

5. The capsule of claim 4, wherein at least six ultrasonic transducers are included in the array.

6. The capsule of claim 1, wherein the connector includes conductive pins and/or sockets for providing the removable connection.

7. The capsule of claim 1, further comprising multiple directional ultrasonic transducers, electrically connected to the transceiver, arranged to provide 2 pi steradians of solid angle coverage about the capsule.

8. The capsule of claim 7, wherein each of the transducers is configured and arranged to provide approximately a steradian or more of solid angle coverage over a different sector of the 2 pi steradians of solid angle coverage.

9. The capsule of claim 1, wherein the payload device, microprocessor unit, transceiver and at least one transducer cooperate to measure a physiological condition within the body, convert information about said physiological condition into a data stream, and transmit said data stream via a signal to a position outside the body.

10. A system for wireless communication with a transceiver within a living body, the system comprising:
  a) at least two capsules each configured and dimensioned to be ingestible and/or implantable in an animal body, each capsule including:
    a payload device selected from the group consisting of medical diagnostic devices, devices for treating a medical condition and visualizing apparatus;
    a two-way ultrasonic transducer array;
    a transceiver connected to the transducer array;
    a power supply; and
    a microprocessor,
    wherein the at least two capsules are configured for networked communication with each other using ultrasonic signals,
    wherein each of the networked capsules is identified by a unique identity (ID) address or a unique acoustic frequency, and
    wherein the networked communication includes a two capsule handshake procedure wherein one of the capsules periodically initiates transmission and the other capsule responds directly by acknowledging receipt of the initiated transmission; and,
  b) means positioned external to the body for transmitting and receiving ultrasonic signals to and from at least one of the at least two capsules.

11. The system of claim 10, where in the means external to the body further comprises means for transmitting radio frequency electromagnetic signals and the system further comprises a remote monitoring station for receiving said radio frequency electromagnetic signals.

12. The system of claim 10, wherein the transducer array includes a two-way ultrasonic transducer array ranged to provide 2 pi steradians of solid angle coverage about the capsule.

* * * * *